United States Patent
Liu et al.

(10) Patent No.: US 11,098,065 B2
(45) Date of Patent: Aug. 24, 2021

(54) PREPARATION METHOD OF AN ENERGETIC COORDINATION COMPOUND WITH 5-METHYLTETRAZOLE

(71) Applicant: Ningxia University, Yinchuan (CN)

(72) Inventors: Xiangyu Liu, Yinchuan (CN); Huiliang Zhou, Yinchuan (CN); Jinhui Yang, Yinchuan (CN); Xiaohui Ma, Yinchuan (CN); Senni Cao, Yinchuan (CN)

(73) Assignee: Ningxia University, Yinchan (CN)

( * ) Notice: Subject to any disclaimer, the term of this patent is extended or adjusted under 35 U.S.C. 154(b) by 0 days.

(21) Appl. No.: 16/985,713

(22) Filed: Aug. 5, 2020

(65) Prior Publication Data

US 2021/0040123 A1   Feb. 11, 2021

(30) Foreign Application Priority Data

Aug. 7, 2019  (CN) .......................... 201910726880.3

(51) Int. Cl.
  *C07F 1/00*  (2006.01)
(52) U.S. Cl.
  CPC .................................. *C07F 1/005* (2013.01)
(58) Field of Classification Search
  None
  See application file for complete search history.

(56) References Cited

PUBLICATIONS

Haiges et al., Dalton Transactions (2015), 44(22), pp. 10166-10176.*

Xue et al., Inorganic Chemistry (2004), 43(25), pp. 7972-7977.*
Xue et al., Chemistry of Materials (2005), 17(1), pp. 191-198.*
Tao Wu et. al, "Effect of substituted groups of ligand on construction of topological networks: In situ generated silver(!) tetrazolate coordination polymers", published in Inorganic Chemistry communications 9 (2006) 341-345 on Feb. 9, 2006.
Yuangang Xu et al. "In situ synthesized 3D metal-organic frameworks (MOFs) constructed from transition metal cations and tetrazole derivatives: a family of insensitive energetic materialst", published in Dalton Transactions, 2017, DOI: 10.1039/C7DT02582C.
Xian-Ming Zhang et al., "Syntheses and structures of metal tetrazole coordination polymer", published in Dalton Transactions, 2006, DOI: 10.1039/b518052j.

* cited by examiner

*Primary Examiner* — Brian J Davis
(74) *Attorney, Agent, or Firm* — Thomas|Horstemeyer

(57) ABSTRACT

The present disclosure discloses a preparation method of a energetic metal coordination compound with 5-methyltetrazole, belonging to the technical field of energetic metal coordination compounds. The method comprises: dissolving methyltetrazole in distilled water, and adding a nitrate therein, to obtain a mixture; stirring the mixture for 30 min, then putting the mixture into a teflon-lined reactor, and reacting at a constant temperature of $120\pm1°$ C. for 72 h, to obtain a crude reaction product; cooling the crude reaction product to 80° C., thermally insulating for 12 h, and hereafter cooling to room temperature at a rate of 3° C./h, to obtain a target product. The coordination compound has a good explosion heat, high thermal stability, and low mechanical sensitivity. The present disclosure could obtain a product with a high yield by a green and environment-friendly method.

9 Claims, 2 Drawing Sheets

PREPARATION METHOD OF AN ENERGETIC COORDINATION COMPOUND WITH 5-METHYLTETRAZOLE

TECHNICAL FIELD

The disclosure relates to the technical field of the preparation of energetic metal coordination compounds, and particularly to a preparation method of a energetic metal coordination compound with 5-methyltetrazole.

BACKGROUND

Energetic materials include explosives, propellants and fireworks, etc., which are widely used in various fields, such as aerospace propellants, mining engineering, pyrotechnics, etc. With the increasing use of energetic materials, their requirements are constantly changing. The pursuit of high energy has gradually evolved into the pursuit of "safety, green, high energy, and high density". Energetic metal complexes have the advantages of high density, good thermal stability, excellent mechanical strength and hardness, etc., and thus can better meet the requirements of high energy and insensitivity, and will become a new generation of energetic materials. According to literature reports, most of the metal complexes with energetic properties have a nitrogen-rich ligand such as triazole/tetrazole. The nitrogen-rich ligand can form energetic metal coordination polymers with metallic silver ions, and their metal-organic framework structure usually has the characteristics of low mechanical sensitivity and high thermal stability.

At present, in the synthesis method of this type of complex, a solvent required is an organic solvent, and the reaction is carried out at a high temperature, and the yield is generally low. For example, Li Dan et al. (Inorganic Chemistry Communications, 2006, 9, 341) used sodium azide and silver nitrate in a mixed solvent of acetonitrile and methanol to react in situ at 140° C. for 3 days, obtaining the complex [Ag(Mtta)]$_n$ with a yield of 35%. Zhang Xianming et al. (Dalton Transactions, 2006, 26, 3170) used sodium azide and silver nitrate in a mixed solvent of dimethylformamide and acetonitrile to react in situ at 150° C. for 3 days, obtaining the complex [Ag(Mtta)]$_n$ with a yield of 40%. Lu Ming et al. (Dalton Transactions, 2017, 46, 11046) used sodium azide and silver nitrate in a mixed solvent of water and acetonitrile to react in-situ at 120° C. for 2 days, obtaining the complex [Ag(Mtta)]$_n$ with a yield of 73%.

SUMMARY

An object of the present disclosure is to provide a green and environment-friendly method for preparing an energetic metal complex with a high purity and yield, to solve the above existing problem of the prior art.

In order to achieve the above purpose of the present disclosure, the present disclosure provides the following technical solutions:

The present disclosure provides a preparation method of a energetic metal coordination compound with 5-methyltetrazole, comprising:

(1) dissolving a 5-methyltetrazole compound in a solvent, and adding a nitrate therein, to obtain a mixture, (2) stirring the mixture obtained in step (1) at room temperature for a period of time, then putting the mixture into a teflon-lined reactor, and reacting at a constant temperature for a period of time, to obtain a crude reaction product; and (3) cooling the crude reaction product obtained in step (2), thermally insulating for a period of time, and hereafter cooling to room temperature, to obtain a target product.

As a further improvement of the present disclosure, the solvent in step (1) is distilled water.

As a further improvement of the present disclosure, the nitrate in step (1) is silver nitrate.

As a further improvement of the present disclosure, a molar ratio of the 5-methyltetrazole compound to the nitrate is 1:1-1:2.

As a further improvement of the present disclosure, a molar ratio of the 5-methyltetrazole compound to the nitrate is 1:1.5.

As a further improvement of the present disclosure, the stirring in step (2) is carried out at room temperature for 30 min.

As a further improvement of the present disclosure, a reaction in the reactor in step (2) is carried out at a temperature of 120±1° C. for 70-72 h.

As a further improvement of the present disclosure, in step (3), the crude reaction product obtained in step (2) is cooled to a temperature of 80±2° C., and thermally insulated for 10 h.

As a further improvement of the present disclosure, in step (3), the cooling to room temperature is carried out at a rate of 3° C./h.

The present disclosure have the following effects:

The target product prepared with the method of the present disclosure has a high purity and yield. Moreover, in the method of the present disclosure, distilled water, used as a solvent, can effectively dissolve 5-methyltetrazole, and the operation "cooling to 80° C. and thermally insulating for a period of time, hereafter cooling" can ensure the sufficient dissolution of excess 5-methyltetrazole or metal-salt. The operation "cooling to room temperature at a rate of 3° C./h" can effectively improve the effect of precipitation and crystallization of the product, and the rate is an optimum cooling rate to obtain a product with the highest yield. A different solubility of 5-methyltetrazole in water from that in other solvents realizes that a energetic metal coordination compound with 5-methyltetrazole with a high purity and yield can be prepared in a short time by using a hydrothermal method.

The energetic metal coordination compound with 5-methyltetrazole prepared in the present disclosure has a yield of above 90%, and a purity of above 99.9%. The combustion heat of the coordination compound is measured by an oxygen bomb calorimeter, and the production heat thereof is calculated. A combustion reaction equation is written, and the explosion heat of the metal coordination compound is calculated in combination with the Kamlet-Jacobs equation to be 0.316 kcal·g$^{-1}$. The thermogravimetric analysis shows that the complex has a good thermal stability (a decomposition temperature of 354° C.). Measurement results of a sensitivity meter show that the complex has a good mechanical sensitivity (an impact sensitivity larger than 40 J, and a friction sensitivity larger than 360 N), and thus the complex can be used as a substitute of new energetic materials.

DETAILED DESCRIPTION OF THE EMBODIMENTS

The technical solutions in the embodiments of the present disclosure are described clearly and completely below. Obviously, the described embodiments are only a part of the embodiments of the present disclosure, rather than all the embodiments. Based on the embodiments of the present disclosure, all other embodiments obtained by those ordinary skilled in the art without creative work shall fall within the protection scope of the present disclosure.

EXAMPLE 1

8.4 mg (0.1 mmol) of 5-methyltetrazole (Mtta) was dissolved in 6 mL of distilled water, and then 25.5 mg (0.15 mmol) of $AgNO_3$ was added therein. After being stirred for 30 min, the mixture was put into a 15 mL teflon-lined reactor, and reacted at a constant temperature of 119° C. for 72 h. Then, the resulting crude reaction product was cooled to 80° C., thermally insulated for 12 h, and hereafter was cooled to room temperature at a rate of 3° C./h, to obtain the target product energetic metal coordination compound with 5-methyltetrazole, with a yield of 92% and a purity of 99.9%.

Figure 1:
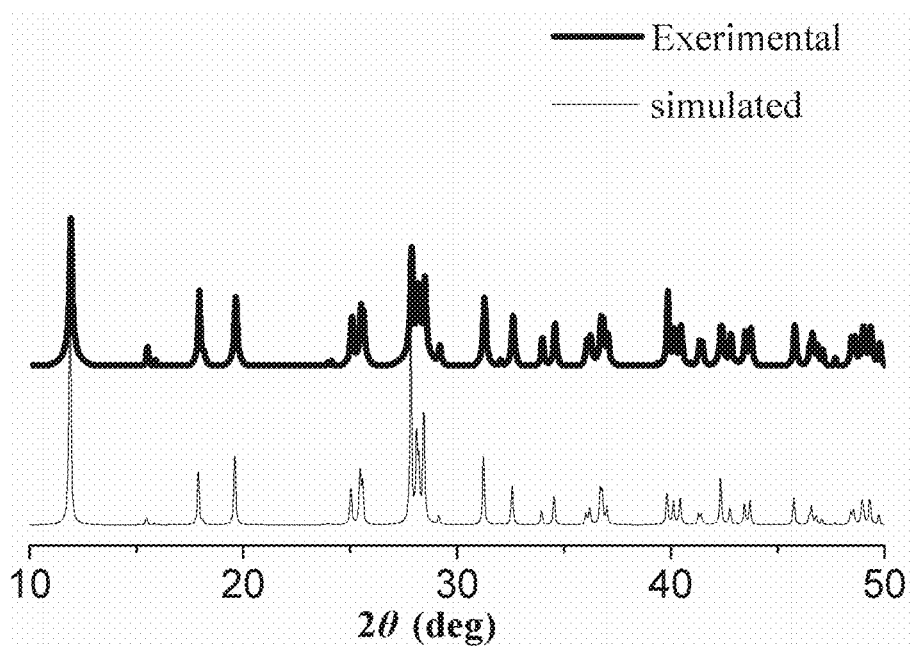
FIG. 1 is a powder diffraction pattern of the energetic metal coordination compound with 5-methyltetrazole prepared in Example 1 of the present disclosure.
Figure 2:
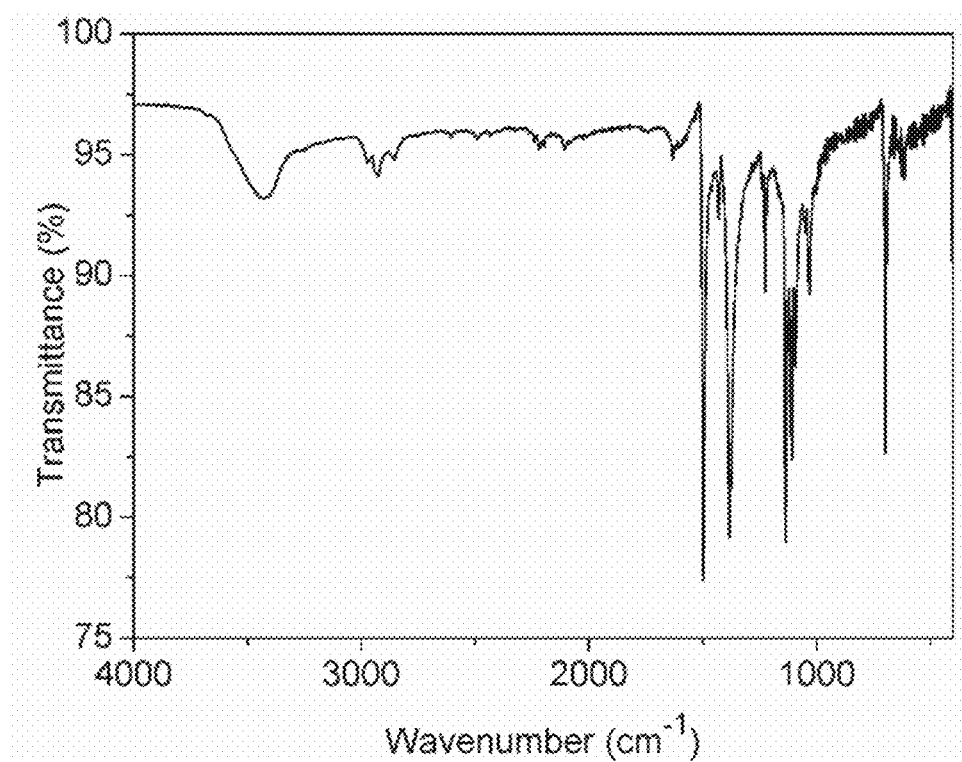
FIG. 2 is an infrared spectrum diagram of the energetic metal coordination compound with 5-methyltetrazole prepared in Example 1 of the present disclosure.
Figure 3:
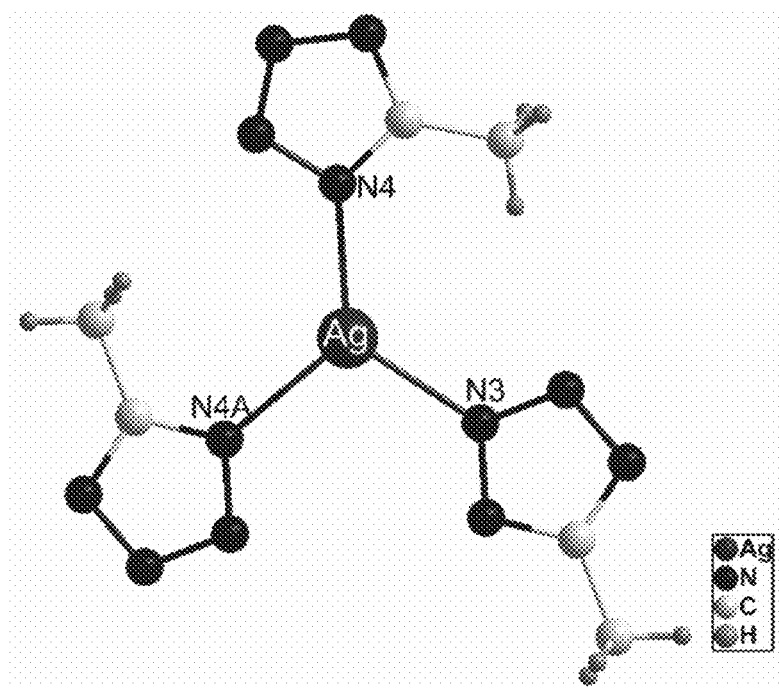
FIG. 3 is a diagram of the crystal structure of the energetic metal coordination compound with 5-methyltetrazole prepared in Example 1 of the present disclosure, measured by an X-ray single crystal diffractometer.
Figure 4:
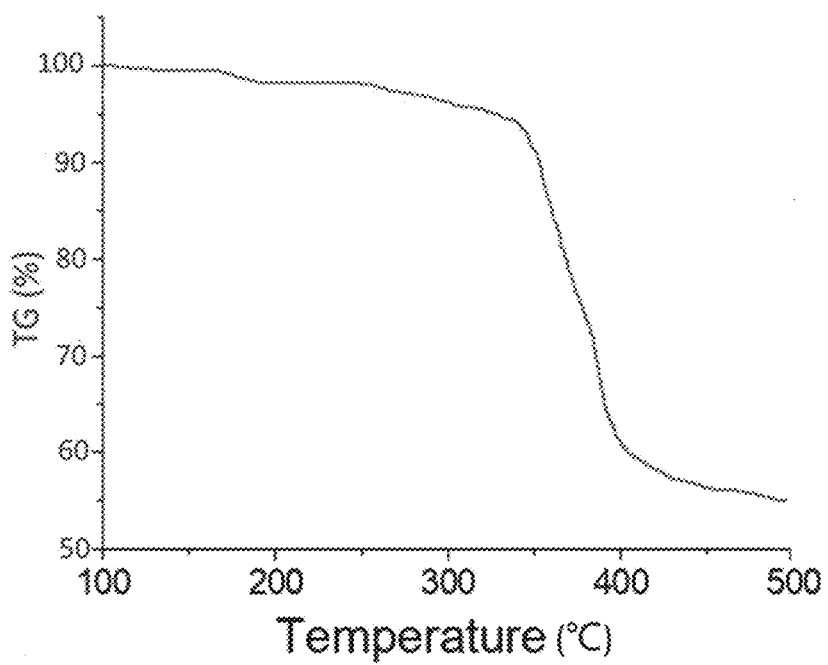
FIG. 4 is a thermogravimetric analysis diagram of the energetic metal coordination compound with 5-methyltetrazole prepared in Example 1 of the present disclosure.

The powder diffraction pattern of the energetic metal coordination compound with 5-methyltetrazole prepared in this Example was shown in FIG. 1, and the infrared spectrum diagram thereof was shown in FIG. 2. From FIG. 1 and FIG. 2, it can be seen that the obtained compound was $[Ag(Mtta)]_n$. The crystallographic data of the energetic metal coordination compound with 5-methyltetrazole prepared in this example was shown in Table 1. The combustion heat of the coordination compound prepared in this example was measured by an oxygen bomb calorimeter, and the production heat thereof was calculated. A combustion reaction equation was written, and the explosion heat of the metal coordination compound was calculated in combination with the Kamlet-Jacobs equation to be 0.316 $kcal \cdot g^{-1}$. Thermogravimetric analysis shows that the complex has a good thermal stability (a decomposition temperature of 354° C.). Measurement results of a sensitivity meter show that the complex has a good mechanical sensitivity (a impact sensitivity larger than 40 J, and a friction sensitivity larger than 360 N), and thus the complex can be used as a substitute of new energetic materials.

TABLE 1

| Empirical formula | $AgC_2N_4H_3$ |
| --- | --- |
| Formula weight | 190.94 |
| Temperature/K | 100(2) |
| Crystal system | Triclinic |
| Space group | P-1 |
| a (Å) | 7.4827(12) |
| b (Å) | 7.5683(8) |
| c (Å) | 7.5707(8) |
| α (°) | 98.201(9) |
| β (°) | 95.954(11) |
| γ (°) | 95.966(11) |
| V (Å$^3$) | 418.98(9) |
| Z | 2 |
| D (Mg/m$^3$) | 3.027 |
| Mu (mm$^{-1}$) | 4.643 |
| F(0 0 0) | 360 |
| Unique reflections | 1574 |
| Observed reflections | 1938 |
| $R_{int}$ | 0.0452 |
| Data/restraints/parameters | 1938/14/129 |
| Final R indices[I > 2σ(I)] | $R_1 = 0.0529$<br>$wR_2 = 0.1360$ |
| R indices (all data) | $R_1 = 0.0620$<br>$wR_2 = 0.1426$ |
| Goodness-of-fit on F$^2$ | 1.069 |

EXAMPLE 2

8.4 mg (0.1 mmol) of methyltertazole (Mtta) was dissolved in 6 mL of distilled water, and then 17.0 mg (0.1 mmol) of $AgNO_3$ was added therein; that is to say, a molar ratio of Mtta to $AgNO_3$ is 1:1. After being stirred for 30 min, the mixture was put into a 15 mL teflon-lined reactor, and reacted at a constant temperature of 119° C. for 71 h. Then, the resulting crude reaction product was cooled to 80° C., thermally insulated for 12 h, and hereafter was cooled to room temperature at a rate of 3° C./h, to obtain the target product energetic metal coordination compound with 5-methyltetrazole, with a yield of 90% and a purity of 99.9%.

EXAMPLE 3

8.4 mg (0.1 mmol) of methyltertazole (Mtta) was dissolved in 6 mL of distilled water, and then 34.0 mg (0.2 mmol) of $AgNO_3$ was added therein; that is to say, a molar ratio of Mtta to $AgNO_3$ is 1:2. After being stirred for 30 min, the mixture was put into a 15 mL teflon-lined reactor, and reacted at a constant temperature of 121° C. for 70 h. Then, the resulting crude reaction product was cooled to 82° C., and thermally insulated for 12 h, hereafter was cooled to room temperature at a rate of 3° C./h, to obtain the target product energetic metal coordination compound with 5-methyltetrazole, with a yield of 91% and a purity of 99.9%.

EXAMPLE 4

The preparation method was similar to that of Example 1, expect that a mixed solvent of acetonitrile and methanol with a volume ratio of 1:1 was used as the solvent, to obtain the final product with a yield of 40%, and a purity of 90%.

EXAMPLE 5

The preparation method was similar to that of Example 1, expect that a mixed solvent of acetonitrile and water with a volume ratio of 1:1 was used as the solvent, to obtain the final product with a yield of 72%, and a purity of 82%.

EXAMPLE 6

The preparation method was similar to that of Example 1, expect that the cooling to room temperature was carried out at a rate of 5° C./h, to obtain the target product with a yield of 50%, and a purity of 95%.

EXAMPLE 7

The preparation method was similar to that of Example 1, expect that the cooling to room temperature was carried out at a rate of 1° C./h, to obtain the target product with a yield of 72%, and a purity of 98%.

The above-mentioned embodiments only describe the preferred embodiments of the present disclosure, and do not limit the scope of the present disclosure. Without departing from the design spirit of the present disclosure, those ordinary skilled in the art could made various variations and improvements, and they should fall within the protection scope defined by the claims of the present disclosure.

The invention claimed is:

1. A preparation method of an energetic metal coordination compound with 5-methyltetrazole, comprising:
    (1) dissolving 5-methyltetrazole compound in a solvent, and adding a nitrate therein, to obtain a mixture,
    (2) stirring the mixture obtained in step (1) at room temperature for a period of time, then putting the mixture into a teflon-lined reactor, and reacting at a constant temperature for a period of time, to obtain a crude reaction product;
    (3) cooling the crude reaction product obtained in step (2), thermally insulating for a period of time, and hereafter cooling to room temperature, to obtain the energetic metal coordination compound with 5-methyltetrazole.

2. The preparation method of an energetic metal coordination compound with 5-methyltetrazole of claim 1, wherein the solvent in step (1) is distilled water.

3. The preparation method of an energetic metal coordination compound with 5-methyltetrazole of claim 1, wherein the nitrate in step (1) is silver nitrate.

4. The preparation method of an energetic metal coordination compound with 5-methyltetrazole of claim 1, wherein a molar ratio of 5-methyltetrazole compound to the nitrate in step (1) is 1:1-1:2.

5. The preparation method of an energetic metal coordination compound with 5-methyltetrazole of claim 1, wherein a molar ratio of 5-methyltetrazole compound to the nitrate in step (1) is 1:1.5.

6. The preparation method of an energetic metal coordination compound with 5-methyltetrazole of claim 1, wherein the stirring in step (2) is carried out at room temperature for 30 min.

7. The preparation method of an energetic metal coordination compound with 5-methyltetrazole of claim 1, wherein a reaction in the reactor in step (2) is carried out at a temperature of 120±1° C. for 70-72 h.

8. The preparation method of an energetic metal coordination compound with 5-methyltetrazole of claim 1, wherein in step (3), the crude reaction product obtained in step (2) is cooled to a temperature of 80±2° C., and thermally insulated for 10 h.

9. The preparation method of an energetic metal coordination compound with 5-methyltetrazole of claim 1, wherein in step (3), the cooling to room temperature is carried out at a rate of 3° C./h.

* * * * *